United States Patent [19]

Miller et al.

[11] Patent Number: 5,681,948

[45] Date of Patent: Oct. 28, 1997

[54] TWO-STAGE METHOD FOR PREPARING POLYOL FATTY ACID POLYESTERS

[75] Inventors: Mark Stuart Miller, Arlington Heights; Leslie George West, Glencoe; Robert Charles Dinwoodie, Glenview; Richard S. Silver, Wilmette, all of Ill.

[73] Assignee: Kraft Foods, Inc., Northfield, Ill.

[21] Appl. No.: 398,749

[22] Filed: Mar. 6, 1995

[51] Int. Cl.[6] .................... C07H 13/02; C07H 13/04; C07H 13/06; C07H 1/00

[52] U.S. Cl. .................... 536/115; 536/116; 536/119; 536/120; 536/124

[58] Field of Search ................... 536/115, 116, 536/119, 120, 124

[56] References Cited

U.S. PATENT DOCUMENTS

| | | | |
|---|---|---|---|
| 3,597,417 | 8/1971 | Myhre | 536/119 |
| 4,104,464 | 8/1978 | James | 536/115 |
| 4,298,730 | 11/1981 | Galleymore et al. | 536/119 |
| 4,334,061 | 6/1982 | Bossier, III | 536/119 |
| 4,377,685 | 3/1983 | Bouniot et al. | 536/119 |
| 4,517,360 | 5/1985 | Volpenhein | 536/124 |
| 4,518,772 | 5/1985 | Volpenhein | 536/119 |
| 4,611,055 | 9/1986 | Yamamoto et al. | 536/127 |
| 4,683,299 | 7/1987 | Kea et al. | 536/119 |
| 4,840,815 | 6/1989 | Meyer et al. | 426/611 |
| 4,877,871 | 10/1989 | Klemann et al. | 536/119 |
| 4,897,474 | 1/1990 | Bickert | 536/119 |
| 4,931,552 | 6/1990 | Gibson et al. | 536/124 |
| 4,942,228 | 7/1990 | Gibson | 536/119 |
| 4,952,687 | 8/1990 | Bodor et al. | 536/119 |
| 4,954,621 | 9/1990 | Masaoka et al. | 536/115 |
| 4,966,966 | 10/1990 | Wada et al. | 536/124 |
| 4,968,791 | 11/1990 | Van Der Plank | 536/120 |
| 4,973,682 | 11/1990 | Willemse | 536/115 |
| 5,006,648 | 4/1991 | Van Der Plank et al. | 536/119 |

(List continued on next page.)

FOREIGN PATENT DOCUMENTS

| | | |
|---|---|---|
| 0 254 376 | 1/1988 | European Pat. Off. . |
| A-0311154 | 4/1989 | European Pat. Off. . |
| 0 322 971 | 7/1989 | European Pat. Off. . |
| 0 323 670 | 7/1989 | European Pat. Off. . |
| 0 349 059 | 1/1990 | European Pat. Off. . |
| 0 383 404 | 8/1990 | European Pat. Off. . |
| 227137A1 | 3/1984 | Germany . |
| WO 92/00947 | 1/1992 | WIPO . |
| WO92/03060 | 5/1992 | WIPO . |

OTHER PUBLICATIONS

Bailey, "Bailey's Industrial Oil & Fat Products", 1964, pp. 958–972.

*Primary Examiner*—John Kight
*Assistant Examiner*—Everett White
*Attorney, Agent, or Firm*—Fitch, Even, Tabin & Flannery

[57] ABSTRACT

A two-stage method for the preparation of polyol fatty acid polyesters is provided. The resulting polyol fatty acid polyesters are very lightly colored (i.e., colorless to slightly yellow) and have a high degree of substitution with fatty acid groups. The first stage of this two-stage method is a solvent-based esterification reaction; the second stage is an essentially solvent-free esterification reaction. In the first stage, a polyol in a solvent (e.g., sucrose in dimethylsulfoxide)) is reacted with fatty acid lower alkyl esters at relatively low temperatures using an alkaline salt catalyst. After the desired degree of esterification is obtained, the resulting partially-esterified polyol fatty acid polyesters and the solvent-containing phase are separated. The separated partially-esterified polyol fatty acid polyesters are further esterified with the same or different fatty acid lower alkyl esters in a second stage with an alkaline salt catalyst using essentially solvent-free, high temperature conditions whereby the degree of substitution is significantly increased. Most of the color bodies and other contaminants capable of producing color are removed with the solvent in the first stage and, therefore, are not present during the higher temperature reaction conditions of the second stage. The resulting polyol fatty acid polyesters, and in particular the sucrose fatty acid polyesters, are especially useful as fat substitutes in food applications and products.

42 Claims, 2 Drawing Sheets

U.S. PATENT DOCUMENTS

| | | | |
|---|---|---|---|
| 5,008,387 | 4/1991 | Matsumoto et al. | 536/120 |
| 5,043,438 | 8/1991 | Buter | 536/127 |
| 5,055,571 | 10/1991 | Van Lookeren | 536/124 |
| 5,071,975 | 12/1991 | Van Der Plank et al. | 536/119 |
| 5,079,355 | 1/1992 | Meszaros Grechke et al. | 536/119 |
| 5,144,023 | 9/1992 | Willemse | 536/124 |
| 5,194,281 | 3/1993 | Johnston et al. | 426/531 |
| 5,225,049 | 7/1993 | Barmentlo et al. | 536/119 |
| 5,231,199 | 7/1993 | Willemse | 554/174 |
| 5,239,097 | 8/1993 | Wolf et al. | 554/190 |
| 5,250,155 | 10/1993 | Zwanenburg et al. | 536/119 |

├──┤ 25μm

├──┤ 50μm

5,681,948

TWO-STAGE METHOD FOR PREPARING POLYOL FATTY ACID POLYESTERS

FIELD OF THE INVENTION

This invention provides a two-stage method for the preparation of polyol fatty acid polyesters, especially saccharide fatty acid polyesters, and most especially sucrose fatty acid polyesters. The polyol fatty acid polyesters produced by the method of this invention are very lightly colored (i.e., colorless to slightly yellow) and have a high degree of substitution with fatty acid groups. The first stage of this two-stage method is a solvent-based esterification reaction; the second stage is an essentially solvent-free esterification reaction. In the first stage, a polyol or saccharide in a solvent (e.g., sucrose in dimethylsulfoxide) is reacted with fatty acid lower alkyl esters at relatively low temperatures using an alkaline salt catalyst. After the desired degree of esterification is obtained, the resulting partially-esterified polyol fatty acid polyester-containing phase and the solvent-containing phase are separated. The separated partially-esterified polyol fatty acid polyesters are further esterified with the same or different fatty acid lower alkyl esters in a second stage with an alkaline salt catalyst using essentially solvent-free, high temperature conditions whereby the degree of substitution is significantly increased. Most of the color bodies and other contaminants capable of producing color are removed with the solvent in the first stage and are not, therefore, present during the higher temperature reaction conditions of the second stage. Using sucrose as an example, almost colorless sucrose fatty acid polyesters having 70 percent or greater sucrose fatty acid octaesters can be prepared by the method of this invention. The polyol or saccharide fatty acid polyesters, and especially the sucrose fatty acid polyesters, produced by the improved method of this invention are especially useful as fat substitutes in food applications and products.

BACKGROUND OF THE INVENTION

The human consumption of fats in various foodstuffs contributes significantly to obesity. High fat diets also contribute to various human diseases such as heart and coronary artery diseases. One method of reducing obesity and/or diseases such as heart and coronary artery diseases in the human population is to reduce the consumption of fat. In recent years, fat substitutes or low-calorie fats have attracted increasing attention as a method of reducing the fat and calorie content of foodstuffs. The objective is to provide edible fats with reduced absorption and digestive properties with minimal side effects and with acceptable taste and mouthfeel characteristics when incorporated into food compositions.

Transesterification reactions have been used to prepare saccharide polyesters with reduced absorption and digestive properties. Such direct transesterification reactions generally employed high temperatures and solvents (such as dimethylacetamide, dimethylformamide, dimethylsulfoxide, and the like). The resulting saccharide polyesters were generally very darkly colored and often contained unacceptable levels of solvent. Decolorization and removal of solvent could often not be accomplished to the degree or level required for use in food products. Moreover, such direct transesterification methods generally did not result in essentially fully-esterified fatty acid polyesters.

More recently, Meyer et al., U.S. Pat. No. 4,840,815 (issued Jun. 20, 1989), and Meyer et al., PCT Publication WO 92/0360 (published Mar. 5, 1992), provided a one-stage, solvent-free, low-temperature, low-pressure process for the preparation of saccharide fatty acid polyesters. The Meyer et al. process involves reacting a mixture of a lower acyl ester saccharide, a fatty acid lower alkyl ester, and an alkali metal catalyst at a reaction temperature of 100° to 125° C. while drawing a vacuum of less than about 15 torr over the reaction mixture. The saccharide fatty acid polyesters are reported to be formed via a transesterification reaction whereby at least a portion of the lower acyl ester groups on the starting saccharide are replaced with the fatty acid groups from the fatty acid lower alkyl ester. The transesterification catalysts employed were alkali metals, with sodium and potassium metals the most preferred. At the reaction temperature, the alkali metal catalysts were molten.

In addition to the transesterification catalysts used by Meyer et al. (i.e., elemental alkali metals), other basic transesterification catalysts are known for the preparation of saccharide fatty acid esters from the saccharides. Such basic transesterification catalysts include alkali metal carbonates, alkali metal hydroxides, and alkali metal alkoxides. Yamamoto et al., U.S. Pat. No. 4,611,055 (issued Sep. 9, 1986), report that the alkali metal carbonate and alkali metal hydroxide catalysts generally provide higher yields than the alkali metal alkoxide catalysts. Volpenhein, U.S. Pat. No. 4,517,360 (issued May 14, 1985), reports that the alkali metal carbonate catalysts provide increased yields and shorter reaction times than the alkali metal hydroxide and alkali metal alkoxide catalysts. These basic transesterification catalysts (i.e., alkali metal carbonates, hydroxides, and alkoxides) generally require higher reaction temperatures (on the order of 180° C.) than the alkali metal catalysts of Meyer et al. Moreover, the transesterification methods and catalysts of Yamamoto et al. and Volpenhein generally require a fatty acid metal soap to insure a homogeneous reaction mixture. Such fatty acid metal soaps are not used or required in the Meyer et al. method. Mieth et al., German Patent 227,137 A1 (laid open Sep. 11, 1985), provides a method for preparing polyol-ester mixtures suitable for use as fat substitutes whereby saccharides are esterified or transesterified with short-chain carboxylic acid derivatives in the presence of a catalyst and then reacted with triglycerides having long-chain carboxylic acid derivatives (i.e., pig grease or hard rape fat) at a temperature of 120° to 140° C. The polyol-ester mixtures so produced can be subjected to further transesterification reactions at 100° to 120° C. using long-chain carboxylic acids or their esters as reagents. The catalysts used by Mieth et al. include phosphorous acid, alkali metals, alkali alkylates, and alkali salts of weak acids.

Each of these known solvent and solvent-free esterification methods results in saccharide fatty acid polyesters which are highly colored (i.e., strongly yellow to dark brown or even black). Often these products are so darkly colored than standard decolorization procedures cannot yield suitable saccharide fatty acid polyester products. Moreover, each of these known solvent and solvent-free esterification methods results in saccharide fatty acid polyesters which contain significant levels of less than fully-esterified products. Using sucrose fatty acid polyesters as an example, the known solvent and solvent-free esterification methods generally provide sucrose fatty acid octaesters at levels less than about 60 percent (and often much less than 60 percent). It would be desirable, therefore, to provide lightly-colored polyol or saccharide fatty acid polyesters in good yields that did not require any, or at most only minimal, decolorization treatment. It would also be desirable to provide such lightly-colored polyol saccharide fatty acid polyesters having high levels of essentially fully-esterified polyesters. It would be highly desirable to provide lightly-colored sucrose fatty acid polyesters in good yield and having at least 70 percent, and preferably at least 85 percent, sucrose fatty acid octaesters. The two-stage process of this invention provides such polyol or saccharide fatty acid polyesters and such sucrose fatty acid polyesters.

SUMMARY OF THE INVENTION

The present invention relates to an improved method for preparing polyol fatty acid polyesters and saccharide fatty acid polyesters, especially sucrose fatty acid polyesters, via a two-stage transesterification reaction. The method of this invention provides polyol and saccharide fatty acid polyesters having significantly improved color characteristics (i.e., colorless to light yellow) as compared to polyol and saccharide fatty acid polyesters produced by prior art methods. Moreover, the method of this invention provides polyol and saccharide fatty acid polyesters having significantly higher levels of fully-esterified polyesters as compared to polyol and saccharide fatty acid polyesters produced by prior art methods. The sucrose fatty acid polyesters produced by the improved method of this invention are especially useful as fat substitutes in food applications and products.

The improved process of the present invention involves a first stage wherein the polyol or saccharide is reacted, in a solvent and in the presence of an alkaline salt catalyst, with fatty acid lower alkyl esters to form a partially-esterified polyol or saccharide fatty acid polyester under relatively mild reaction conditions. The partially-esterified polyol or saccharide fatty acid polyesters is then separated from the first-stage reaction mixture and then further esterified with additional fatty acid lower alkyl esters in a solvent-free system and in the presence of an alkaline salt catalyst using more rigorous conditions (i.e., higher temperatures). Color bodies and other contaminants which might form highly-colored products under the more extreme reaction conditions of the second stage appear generally to be removed with the solvent in the first stage and, therefore, are never exposed to the high temperature conditions of the second stage. Although not wishing to be limited by theory, it appears that the removal of these color bodies and other contaminants in the first stage is largely responsible for the excellent color characteristics of the resulting polyol or saccharide fatty acid polyesters of this invention. In addition to improved color characteristics, the method of this invention provides polyol and saccharide fatty acid polyesters having a significantly higher degree of fatty acid esterification than was available from prior art methods. For example, sucrose fatty acid polyesters can be obtained having at least about 70, preferably at least about 85, and most preferably at least about 90, percent octaester content. Generally, we have only been able to obtain octaester contents of less than about 60 percent using prior art methods. Again, not wishing to be limited by theory, the removal of color bodies and other contaminants (including, for example, free organic acids) with the solvent in the first stage may allow the esterification reactions of the second stage to proceed to a greater extent, thereby producing significantly more fatty acid esterified products. At least some evidence suggests that some contaminants (or products resulting therefrom) which might be present in the polyol or saccharide and/or fatty acid lower alkyl ester starting materials may retard fatty acid esterification and thereby prevent more complete esterification of the polyol or saccharide. Nonetheless, and for whatever reason or reasons, the polyol and saccharide fatty acid polyesters of this invention have significantly better color characteristics and significantly higher levels of fully-esterified polyesters than the polyol and saccharide fatty acid polyesters produced by the prior art methods.

One object of the present invention is to provide a method for making a fully-esterified polyol fatty acid polyester, said method comprising a first-stage reaction and a second-stage reaction:

wherein the first-stage reaction comprises:

(1) reacting a polyol having at least four hydroxyl groups with a first fatty acid lower alkyl ester composition in the presence of a first alkaline salt catalyst and a solvent at a reduced pressure and a temperature of less than about 105° C. while removing by-product lower alkyl alcohol until a partially-esterified polyol fatty acid polyester is formed which has, on average, at least 50 percent of the hydroxyl groups in the polyol esterified with fatty acid groups from the first fatty acid lower alkyl ester composition; and (2) separating the partially-esterified polyol fatty acid polyester from the solvent; and wherein the second-stage reaction comprises:

(1) reacting the separated partially-esterified polyol fatty acid polyester with a second fatty acid lower alkyl ester composition, in the presence of a second alkaline salt catalyst and in the absence of any additionally-added solvent, at a reduced pressure and a temperature of greater than about 110° C. while removing by-product lower alkyl alcohol until a fully-esterified polyol fatty acid polyester is formed which contains at least 70 percent by weight polyol fatty acid polyesters in which essentially all hydroxyl groups of the polyol are esterified with fatty acid groups from either the first or second fatty acid lower alkyl ester compositions; and (2) collecting the fully-esterified polyol fatty acid polyester.

Another object of this invention is to provide a method for making a fully-esterified sucrose fatty acid polyester, said method comprising a first-stage reaction and a second-stage reaction:

wherein the first-stage reaction comprises:

(1) reacting sucrose with an excess of a first fatty acid methyl ester composition, in the presence of a first alkaline salt catalyst and a solvent selected from the group consisting of dimethylacetamide, dimethylformamide, and dimethylsulfoxide, at a reduced pressure of about 1 to 50 torr and a temperature of about 60° to 105° C. while removing methanol by-product until a partially-esterified sucrose fatty acid polyester is formed which has, on average, at least 50 percent of the hydroxyl groups in the sucrose esterified with fatty acid groups from the first fatty acid methyl ester composition; and (2) separating the partially-esterified sucrose fatty acid polyester from the solvent; and wherein the second-stage reaction comprises:

(1) reacting the separated partially-esterified sucrose fatty acid polyester with a second fatty acid methyl ester composition, in the presence of a second alkaline salt catalyst and in the absence of any additionally-added solvent, at a reduced pressure of about 0.5 to 50 torr and a temperature of about 110° to 150° C. while removing methanol by-product until a fully-esterified sucrose fatty acid polyester is formed which contains at least 70 percent by weight sucrose fatty acid polyesters in which essentially all hydroxyl groups of the sucrose are esterified with fatty acid groups from either the first or second fatty acid methyl ester compositions; and (2) collecting the fully-esterified sucrose fatty acid polyester.

These and other objects and advantages of the present invention will become apparent through the following description of the drawings and preferred embodiments of the invention.

DESCRIPTION OF THE PREFERRED EMBODIMENTS

Figure 1B:
FIG. 1 contains photomicrographs showing potassium carbonate catalyst added as a dry powder (FIG. 1A) and potassium carbonate catalyst added to the reaction mixture as an aqueous solution under conditions where the water is flashed off immediately or almost immediately upon addition (FIG. 1B).

The method of the present invention provides an improved method for the preparation of polyol and saccharide fatty acid polyesters via a two-stage esterification process. In the first stage of the present method, a polyol or saccharide containing at least four, and preferably at least six, hydroxyl groups is partially esterified with fatty acid groups in a solvent system using fatty acid lower alkyl esters and an alkaline salt catalyst under relative mild conditions while removing, preferably continuously and rapidly, by-product lower alkyl alcohols. The first-stage esterification is continued until at least 50 percent of the hydroxyl groups in the starting polyol or saccharide are esterified with fatty acid groups from the fatty acid lower alkyl esters (i.e., until a partially-esterified polyol or saccharide fatty acid polyester is formed). Preferably, the first-stage esterification is continued until about 60 to 90 percent of the hydroxyl groups in the starting polyol or saccharide are esterified with such fatty acid groups. When sucrose is used as the polyol, the first-stage esterification is preferably continued until the average degree of esterification reaches between about 5 and 7.

At the completion of the first-stage esterification, the partially-esterified polyol or saccharide fatty acid polyester and the solvent are separated using conventional techniques. In most cases, at the completion of the first-stage esterification, the partially-esterified polyol or saccharide fatty acid polyester is contained in the upper phase of the reaction mixture and the solvent is predominately contained in the lower phase. Thus, the separation of the partially-esterified polyol or saccharide fatty acid polyester and the solvent can preferably be effected by simply separating the upper and lower phases. In some cases, addition of water to the reaction mixture can be used to assist or encourage formation of the separate phases, which can then be separated. Using sucrose as the starting material, the separated partially-esterified sucrose fatty acid polyester would normally consist of mainly tetraesters, pentaesters, hexaesters, heptaesters, and octaesters and have a preferred average degree of substitution of about 5 to 7; any trace amounts of monoesters, diesters, and triesters would have a tendency to remain in, and be removed with, the solvent phase. Generally, over 80 percent of the solvent is removed with the lower layer upon separation of the layers. Solvent remaining in the upper layer can, if desired, be removed by distillation of the upper layer. The solvent is preferably treated or cleaned up using conventional techniques (e.g., distillation) for recycling to the first-stage esterification reaction.

The separated partially-esterified polyol or saccharide fatty acid polyesters from the first stage are then subjected to further esterification under more rigorous or harsher conditions in the second stage. Second-stage esterification is an essentially solvent-free esterification, by which is meant that no further solvent is added to the reaction mixture in the second stage. Of course, as one skilled in the art will realize, some solvent from the first stage will likely be present with, or come in with, the partially-esterified saccharide fatty acid polyester; the amount of such solvent will, however, be relatively small and will tend to be removed (via distillation) during the early portion of the second-stage esterification. If water is added in the first stage to assist in the formation of separate polyester and solvent phases, most of the water is removed by separation of the upper and lower phases. Any remaining water can be quickly removed by distillation in the early portion of the second stage. The catalyst can be added as a powder, a suspension, or a solution. Preferably the catalyst is added as an aqueous solution. Water added with such an aqueous solution does not appear to significantly effect subsequent esterification reactions, possibly because the amount added is relatively small and it is almost immediately flashed off and removed from the system.

The second-stage esterification is carried out by reacting the partially-esterified saccharide fatty acid polyesters from the first stage with fatty acid lower alkyl esters in the presence of an alkaline salt catalyst while removing, preferably continuously and rapidly, by-product lower alkyl alcohols. The fatty acid lower alkyl ester reactants in the second stage include freshly added fatty acid lower alkyl esters as well as any first-stage fatty acid lower alkyl esters which may be carried over from the first stage. The fatty acid lower alkyl esters of the second stage may be composed of from 0 to 100 percent of carried-over fatty acid lower alkyl esters from the first stage. The fatty acid lower alkyl esters used in the second stage may be the same as or different from the fatty acid lower alkyl esters used in the first stage. The alkaline salt catalyst used in the second stage may be the same as or different from the alkaline salt catalyst used in the first stage; preferably, the same alkaline salt catalyst is used in both the first and second stages. Most preferably, potassium carbonate is used as the alkaline salt catalyst in both the first and second stages.

The second-stage esterification is continued until a fully-esterified polyol or saccharide fatty acid polyester is obtained. For purposes of this invention, a fully-esterified polyol or saccharide fatty acid polyester is a polyester having at least 70 percent by weight polyol or saccharide fatty acid polyesters in which essentially all hydroxyl groups of the polyol or saccharide are esterified with fatty acid groups from the fatty acid lower alkyl esters used in the first and second stages. Preferably, such a fully-esterified polyol or saccharide fatty acid polyester has at least 85 percent by weight polyesters in which essentially all hydroxyl groups of the polyol or saccharide are esterified with fatty acid groups derived from the fatty acid lower alkyl esters used in the first and second stages. For example, a fully-esterified sucrose fatty acid polyester would contain at least 70 percent by weight, and preferably at least 85 percent by weight, sucrose fatty acid octaesters wherein each of the hydroxyl groups of the starting sucrose are esterified with a fatty acid group. Fully-esterified sucrose fatty acid polyesters containing over 90 percent by weight sucrose fatty acid octaesters, wherein each of the hydroxyl groups of the starting sucrose are esterified with a fatty acid group, have been obtained using the present two-stage process.

The present two-stage process, as well as each individual stage, can be run in a batch, semi-continuous, or continuous mode. Preferably, the present two-stage process is operated in a semi-continuous or continuous mode. Preferably, the present two-stage process is operated such that the solvent used in the first stage and the fatty acid lower alkyl esters used in the first and second stages are recovered and recycled within the process.

The polyol starting materials for the present invention include polyhydroxyl alcohols and saccharides having at least four, and preferably at least six, hydroxyl groups. Suitable polyhydroxyl alcohols include, for example, linear alcohols of the general formula $HOCH_2(CHOH)_nCH_2OH$ where n is an integer equal to or greater than 2. The saccharide starting materials can be monosaccharides, disaccharides, and higher polysaccharides. Suitable monosaccharides include fructose, glucose, galactose, mannose, ribulose, rhamnose, xylulose, xylose, ribose, and arabinose; glucose and galactose are the preferred monosaccharides. Suitable disaccharides include melibiose, lactose, maltose, sucrose, trehalose, and cellobiose; sucrose is the preferred disaccharide. Suitable higher polysaccharides include raffinose, gentiobiose, 4'-galactosyl lactose, trisaccharides of galactose, mannose, glucose, and fructose, stachyose, verbascose, maltodextrins, corn syrup solids, xylans, glycogen, cellulose, amylose, agarose, galactans, and mannans. Sucrose, a non-reducing disaccharide, is the most preferred starting polyol and/or saccharide.

Non-reducing saccharides (such as sucrose) can be used directly in the present invention. Reducing saccharides (i.e., those which form a hemiacetal or hemiketal) should normally be first be converted to a non-reducing form prior to the first-stage initial esterification reaction; such conversion can be carried out using conventional means. Once the non-reducing saccharide is formed, the remaining hydroxy groups may then be treated in the same manner as non-reducing saccharides in the present invention. Both naturally-occurring non-reducing saccharides and non-reducing saccharides prepared from reducing saccharides are employed in the same manner in the present invention.

The fatty acid lower alkyl esters employed in the present invention are of general formula RCOOR' where R is a saturated or unsaturated aliphatic group generally containing from 3 to about 23 carbon atoms and R' is a lower alkyl group having from 1 to about 3 carbon atoms. Preferably, R is a long chain saturated or unsaturated aliphatic group containing between about 7 to 23 carbon atoms and R' is a methyl group. The same or different fatty acid lower alkyl esters can be used in the first and second stages. Using different fatty acid lower alkyl esters in the first and second stages allows the incorporation of very different fatty acid groups in an especially convenient manner. For example, fatty acid lower alkyl esters having relatively short fatty acid groups (e.g., $C_8$ to $C_{10}$ fatty acid groups) can be employed in the first stage and then fatty acid groups having relatively long fatty acid groups (e.g., $C_{12}$ to $C_{22}$ fatty acid groups) can be employed in the second stage to produce a polyol fatty acid polyesters having both short and long fatty acid groups. Relatively short fatty acid groups are preferably introduced in the first stage since such fatty acid lower alkyl esters would have a tendency to distill out of the second-stage reaction mixture because the more rigorous conditions (i.e., lower pressures and the higher temperatures). Other fatty acid groups (i.e., relatively long or intermediate in length) can be introduced in either the first or second stages.

The fatty acid lower alkyl esters are preferably derived from the corresponding fatty acids. Examples of suitable fatty acids for forming the fatty acid lower alkyl esters include butyric, caproic, caprylic, capric, lauric, myristic, myristoleic, palmitic, palmitoleic, stearic, oleic, ricinoleic, linoleic, oleosteric, arachidic, behenic, erucic, arachidonic, and lignoceric acids. Pure fatty acids or naturally-occurring fats and oils (such as, for example, found in soybean, safflower, corn, peanut, and cottonseed oils) can be used. Partially hydrogenated natural fats and oils are particularly suited for use in this invention. The fatty acids can be converted to the corresponding fatty acid lower alkyl esters using conventional methods. Both single fatty acid lower alkyl esters or mixtures of fatty acid lower alkyl esters may be employed in the present invention. Thus, for purposes of this invention, a fatty acid lower alkyl ester composition (for either the first or second stage reaction) includes both single fatty acid lower alkyl esters and mixtures of fatty acid lower alkyl esters.

In contrast to the prior art methods, it is generally not necessary to treat the starting polyols or fatty acid lower alkyl esters to remove organic free acids. In most prior art methods is was generally necessary, or at least highly preferred, to treat the starting reagents to minimize water and organic free acids. In the present two-stage method, it has generally been discovered that fatty acid lower acid esters having relatively high levels of free organic acid (i.e., up to about 0.5 to 0.7 percent by weight) can be used. It appears that such organic free acids are generally removed with the separated solvent layer in the first stage. If desired, of course, conventional methods (e.g., alkali extraction) can be used to remove free organic acids from the reagents used in one or both of the two stages; such removal is not, however, required unless the level of organic free acids is excessive (i.e., generally at levels above about 0.7 percent by weight).

Generally, the fatty acid lower alkyl esters in both the first and second stages are used in excess relative to the free hydroxyl content of the starting polyol in the first stage or of the partially-esterified polyol fatty acid polyester in the second stage. Preferably, the fatty acid lower alkyl esters is present in about 50 percent molar excess, or higher, relative to the free hydroxyls, in both stages. Thus using sucrose with its eight hydroxyl groups as an example, the first stage would contain at least eight moles of fatty acid lower alkyl esters, and preferably at least 12 moles (50 percent excess) of fatty acid lower alkyl esters, for each mole of sucrose. And further assuming that the resulting partially-esterified sucrose fatty acid polyester from the first stage had about one-half of its hydroxyl groups esterified, the second stage would contain at least four moles of fatty acid lower alkyl esters, and preferably at least 6 moles (50 percent excess) of fatty acid lower alkyl esters, for each mole of partially-esterified sucrose fatty acid polyester. Of course, the molar ratios will vary with different polyols and partially-esterified polyol fatty acid polyesters because of the different number of free hydroxyl groups present. Lower or higher molar ratios can be used if desired within the general guidelines provided above.

The catalysts employed in the present invention are alkaline salts such as the alkali metal carbonates, alkaline earth carbonates, alkali metal hydroxides, alkaline earth hydroxides, alkali metal alkoxides, and alkaline earth alkoxides, which are normally employed as transesterification catalysts. Especially preferred catalysts include sodium carbonate and potassium carbonate, with potassium carbonate being the most preferred. Mixtures of catalysts can also be used. The catalyst is generally used in an amount less than about 5 weight percent and preferably in the range of about 0.5 to 2.5 weight percent.

Generally finely-divided catalysts, with their higher surface areas, are preferred. The catalyst may be added as a dry powder, in which case the particle size is preferably in the range of about 10 to 50 microns. The catalyst may also be added as a suspension in an organic solvent. When added as a suspension, the preferably highly powdered catalyst is preferably suspended in the same solvent as used in the first stage reaction. More preferably, especially for addition to the second stage, the catalyst is added as an aqueous solution. When added as an aqueous solution, the concentration of the catalyst in such aqueous solution is normally about 5 to 70 percent, preferably about 5 to 40 percent, and more preferably about 5 to 20 percent, by weight. When added as aqueous solution, the catalyst is preferably added to the reaction mixture at the reaction temperature (i.e., reduced pressure and elevated temperature) so that the water is essentially flashed off, or explodes, almost immediately upon addition. The flashing off or explosion of the water phases results in a highly porous, high surface area, almost "gel-like" catalyst structure.

Figure 1A:
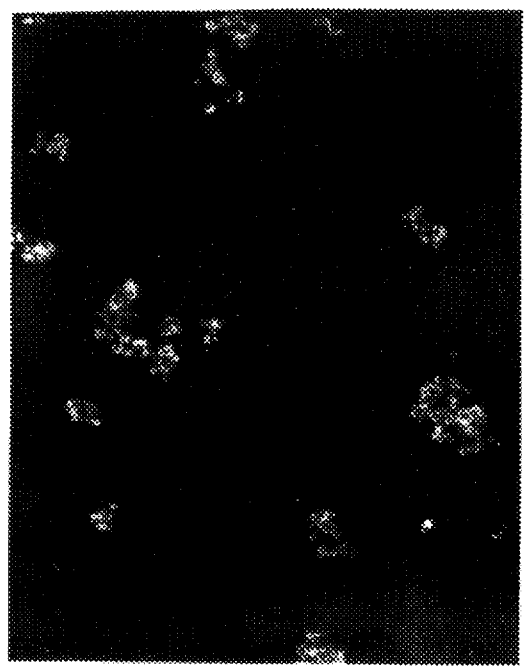

The gel-like structure for a potassium carbonate catalyst added as an aqueous solution to a second-stage reaction system (pressure about 5 torr and temperature about 130° C.) is shown in FIG. 1B. For comparison purposes, a powdered potassium carbonate catalyst is shown in FIG. 1A. The powdered catalyst (FIG. 1A) has discrete and regular particles; the catalyst formed from an aqueous solution (FIG. 1B) has a gel-like structure with "string-like" interconnections. Thus, as illustrated in FIG. 1, the addition of the catalyst as an aqueous solution results in a very different structure which should have a significantly higher surface area. Such a gel-like catalyst provides for significantly greater esterification efficiencies than, for example, the powdered catalyst shown in FIG. 1A. The water added with such an aqueous solution is almost immediately vaporized and is likely removed very quickly from the reaction system (along with any residual solvent from the first stage). Methods by which such aqueous catalyst can be added without breaking or interrupting the reduced pressure in the reaction vessel are generally preferred. For example, the aqueous catalyst solution could be introduced via a catalyst vessel attached (directly or via tubing) to the reaction vessel so that a valve between the catalyst vessel and the reaction vessel can be quickly opened such that a predetermined amount of the aqueous solution is simply and quickly aspirated into the reaction vessel (and preferably below the surface of the reaction mixture). Alternatively, the aqueous catalyst solution could be injected via a septum-covered inlet directly into the reaction vessel (and preferably below the surface of the reaction mixture). Although powdered catalysts can be used, it is generally preferred (especially for the second stage) that the catalyst is added as an aqueous solution so that a catalyst structure similar to that shown in FIG. 1B is obtained.

The first-stage reaction mixture formed from the basic starting materials (polyol, fatty acid lower alkyl ester, solvent, and alkaline salt catalyst) need not be anhydrous or free of organic acids. It is generally preferred, however, that the free organic acid content of the initial reaction mixture be less than about 0.7 percent by weight, or preferably less than about 0.5 percent by weight, based on the weight of the fatty acid lower alkyl esters. Removal of organic acids below these levels can be advantageous (i.e., the first-stage esterification may proceed more smoothly and further) but is not required. Most organic acids present in the first-stage will be removed with the solvent phase and will not, therefore, be carried forward into the second stage.

In the first stage, the reactants (polyol, fatty acid lower alkyl ester, alkaline salt catalyst) and the solvent are mixed in a reaction vessel and heated to the reaction temperature (less than about 105° C. and preferably about 60° to 105° C.) under reduced pressure (about 1 to 50 torr) to form an essentially homogeneous reaction mixture. Preferably, and especially when sucrose is the starting polyol, the reaction temperature is about 85° to 95° C. and the pressure is about 10 to 20 torr; more preferably, the reaction temperature is about 90° C. and the pressure is about 20 torr. The reactants can be added at the same time or sequentially. The reactants can be mixed and then heated to the reaction temperature or some reactants can be added to the other reactants or components (e.g., to the solvent) which is at or close to the reaction temperature. The preferred sequence is to first add the polyol to the solvent and, once dissolution is complete, to add the fatty acid lower alkyl esters followed by the catalyst.

The solvent is added to the first stage in an amount sufficient to achieve a homogeneous solution of polyol at the reaction conditions. Suitable solvents include, for example, dimethylacetamide, dimethylformamide, dimethylsulfoxide, and the like, with dimethylsulfoxide being preferred. The amount of solvent added is not critical so long as sufficient solvent is used to provide an essentially homogenous polyol solution throughout the first-stage esterification. Preferably the reaction conditions during the esterification of this first stage are such that the solvent is maintained under reflux conditions and the by-product lower alkyl alcohol is distilled off. As the esterification reaction proceeds, the relatively low molecular weight, non-fatty acid-containing lower alkyl alcohol by-product is removed to drive the equilibrium esterification. Preferably the by-product alcohol is removed almost as quickly as it is formed. More preferably, the reaction conditions are adjusted to maintain the solvent under reflux conditions whereby a small amount (approximately 2 to 10 percent) of the solvent is removed during the course of the esterification reaction; removal of a portion of the solvent helps to insure complete removal of by-product alcohol during the esterification reaction. If desired, the relatively small amount of distilling solvent (e.g., dimethylsulfoxide) and the by-product alcohol (e.g., methanol) can be separated by first condensing the solvent at room temperature or above and then condensing the alcohol at chilled temperatures (about 10° C. or less). The separated solvent can be recycled directly to the first-stage esterification, or it can be combined with the solvent separated as the solvent phase at the end of the first stage and then recycled.

The first-stage esterification is continued until the partially-esterified polyol fatty acid polyesters are formed. Such partially-esterified polyol fatty acid polyesters have, on average, at least 50 percent of the available hydroxyl groups of the starting polyol esterified with fatty acid groups. More preferably, such partially-esterified polyol fatty acid polyesters have between about 60 and 90 percent of the available hydroxyl groups esterified with fatty acid groups. Using sucrose as an example, preferred partially-esterified sucrose fatty acid polyesters would have an average degree of substitution of at least 5 and, even more preferably, an average degree of substitution between about 5 and 7. Reacting sucrose and fatty acid methyl esters with a potassium carbonate catalyst and dimethylsulfoxide as solvent at about 20 torr and about 90° C., such partially-esterified sucrose fatty acid polyesters can normally be obtained in about 3 to 6 hours reaction time. In some cases, shorter or longer reactions times may be acceptable and even preferred.

Once the first-stage esterification is complete, the partially-esterified polyol fatty acid polyester is separated from the solvent using conventional techniques. In most cases, the partially-esterified polyol fatty acid polyester will be contained predominately in the upper layer of the reaction mixture and the solvent will form a bottom or solvent layer. Thus, the partially-esterified polyol fatty acid polyesters and the solvent can easily be separated using conventional phase separation techniques. In some cases, for example where relatively short chain fatty acid lower alkyl esters are employed in the first stage, the partially-esterified polyol fatty acid polyesters and the solvent will tend not to form separate phases. In such cases, the addition of water to the reaction mixture will often result in the formation of a two phase system, which can then be treated in the same manner as above. Although techniques other than phase separation can be used, the physical separation of the partially-esterified polyol fatty acid polyester phase and the solvent phase is preferred since the solvent phase will generally contain color bodies and other color-producing contaminants that are then effectively removed from the process. Removal of such color bodies and other color-producing contaminants prior to the more rigorous conditions of the second stages apparently allows formation of lighter colored and more highly-esterified polyol fatty acid polyesters in the second stage. It is generally estimated that, in most cases, more than about 80 percent of the solvent will be found in the lower or solvent layer and less than about 20 percent will be associated with the upper or partially-esterified polyol fatty acid polyester layer. It is not necessary to remove the solvent associated with the partially-esterified polyol fatty acid polyester layer before use of the partially-esterified polyol fatty acid polyesters in the second stage. If desired, however, such solvent could be removed using conventional techniques (e.g., distillation) prior to the second stage or during the initial portion of the second stage reaction.

In addition to color bodies and other color-producing contaminants, free acids, and low-esterified polyol fatty acid polyesters will tend to partition or collect in the solvent layer. For example, the separated solvent from the first-stage esterification of sucrose will generally contain color bodies, other color-producing contaminants, and sucrose fatty acid polyesters containing mainly one, two, and three fatty acid ester groups. Preferably the solvent is purified using conventional techniques (e.g., extraction, distillation, and the like) and then recycled to the first-stage esterification process.

The separated partially-esterified polyol fatty acid polyesters from the first stage are then further esterified with fatty acid lower alkyl esters under the more rigorous esterification conditions of the second stage. The partially-esterified polyol fatty polyesters and fatty acid lower alkyl esters generally form a homogeneous reaction mixture at the reaction conditions without the need for a solvent. The alkaline salt catalyst, preferably sodium or potassium carbonate, can be added as a powder, a suspension in an organic solvent, or, more preferably, as an aqueous solution. If added as an aqueous solution, the catalyst preferably should be added to the reactants at, or close to, the desired esterification reaction conditions so that a gel-like catalyst structure (as shown in FIG. 1B) is obtained, and the aqueous carrier is rapidly removed.

The second-stage esterification is carried out at a reaction temperature of greater than about 110° C., and preferably at about 110° to 150° C., and a reduced pressure of about 0.5 to 50 torr while removing by-product lower alkyl alcohol. Preferably, the by-product lower alkyl alcohol is removed continuous and rapidly. Preferably, and especially when sucrose is the starting polyol, the reaction temperature is about 130° C. and the pressure is about 5 torr. During the initial portion of the second-stage esterification, any residual solvent from the first stage (introduced with the partially-esterified polyol fatty acid polyester) can be removed by distillation. This distilled solvent can be recovered, and, if desired, purified and then recycled for reuse in the first-stage.

The second-stage esterification is continued until fully-esterified polyol fatty acid polyesters are obtained. Such fully-esterified polyol fatty acid polyesters contain at least 70 percent by weight polyol fatty acid polyesters in which essentially all hydroxyl groups of the polyol are esterified with fatty acid groups from fatty acid lower alkyl esters of the first-stage and second-stage esterifications. More preferably, such fully-esterified polyol fatty acid polyesters contain at least 85 percent by weight polyol fatty acid polyesters in which essentially all hydroxyl groups of the polyol are esterified with fatty acid groups from fatty acid lower alkyl esters of the first-stage and second-stage esterifications. Using sucrose as an example, such fully-esterified sucrose fatty acid polyesters would contain at least 70 percent sucrose fatty acid octaesters, and preferably at least 85 percent sucrose fatty acid octaesters. Reacting a typical partially-esterified sucrose fatty acid polyesters from a typical first-stage esterification and fatty acid methyl esters with a potassium carbonate catalyst added as an aqueous solution at about 5 torr and about 130° C., such fully-esterified sucrose fatty acid polyesters can normally be obtained in about 6 to 24 hours reaction time. In some cases, shorter or longer reactions times may be acceptable and even preferred.

Once the second stage esterification reaction is completed, the reaction mixture is allowed to cool and the polyol fatty acid polyester is collected and, if desired, purified. Conventional purification techniques can be used. For example, the resulting second-stage reaction mixture could be filtered, extracted with an organic solvent (e.g., methanol, ethanol, isopropanol, mixtures thereof with water, and the like), and then distilled. Although the polyol fatty acid polyesters of this invention are generally only very lightly colored (i.e., colorless to light yellow), they can, if desired, be further decolorized using standard techniques. The desired polyol or saccharide fatty acid polyester can be further purified using conventional techniques including, but not limited to, standard distillation, steam distillation, and molecular distillation.

The amount of solvent (from the first-stage esterification) present in the fully-esterified polyol fatty acid polyesters is generally very low. Most of the solvent (over about 80 percent) is separated from the partially-esterified polyol fatty acid polyesters at the end of the first stage. Of the solvent entering the second stage, most of that solvent can be removed by distillation during the second-stage esterification. The solvent level can be reduced even further during the collection and purification of the fully-esterified polyol fatty acid polyesters from the second stage. Normally, the resulting fully-esterified polyol fatty acid polyesters have solvent levels less than about 2 ppm. If desired, other conventional purification techniques can be used to reduce the residual solvent levels to even lower values.

The by-product lower alkyl alcohol produced in both the first and second stages is preferably removed as quickly as possible once it is formed. Since the by-product alcohol is produced essentially continuously during the esterification reactions in the two stages, its removal is preferably continuous as well. Vacuum techniques, thin-film techniques (e.g., rotary vacuum equipment), and/or inert gas stripping or sparging can be used to remove the by-product as it is formed. Vacuum techniques combined with inert gas stripping or sparging are generally preferred in both the first and second stages. Vacuum techniques combined with vigorous inert gas stripping or sparging are even more preferred. Inert gas sparging at a rate of about 1 to 10 ml/min/g of reactant is generally satisfactory. Suitable inert gases include nitrogen, argon, carbon dioxide, and the like; generally, however, nitrogen is preferred largely on economic considerations. Most preferably, the reactions in both the first and second stages are run under inert, reduced-pressure, streams of the inert gas (preferably nitrogen) at a vacuum lower than about 50 torr for the first stage and a vacuum lower than about 50 torr for the second stage.

Figure 2:
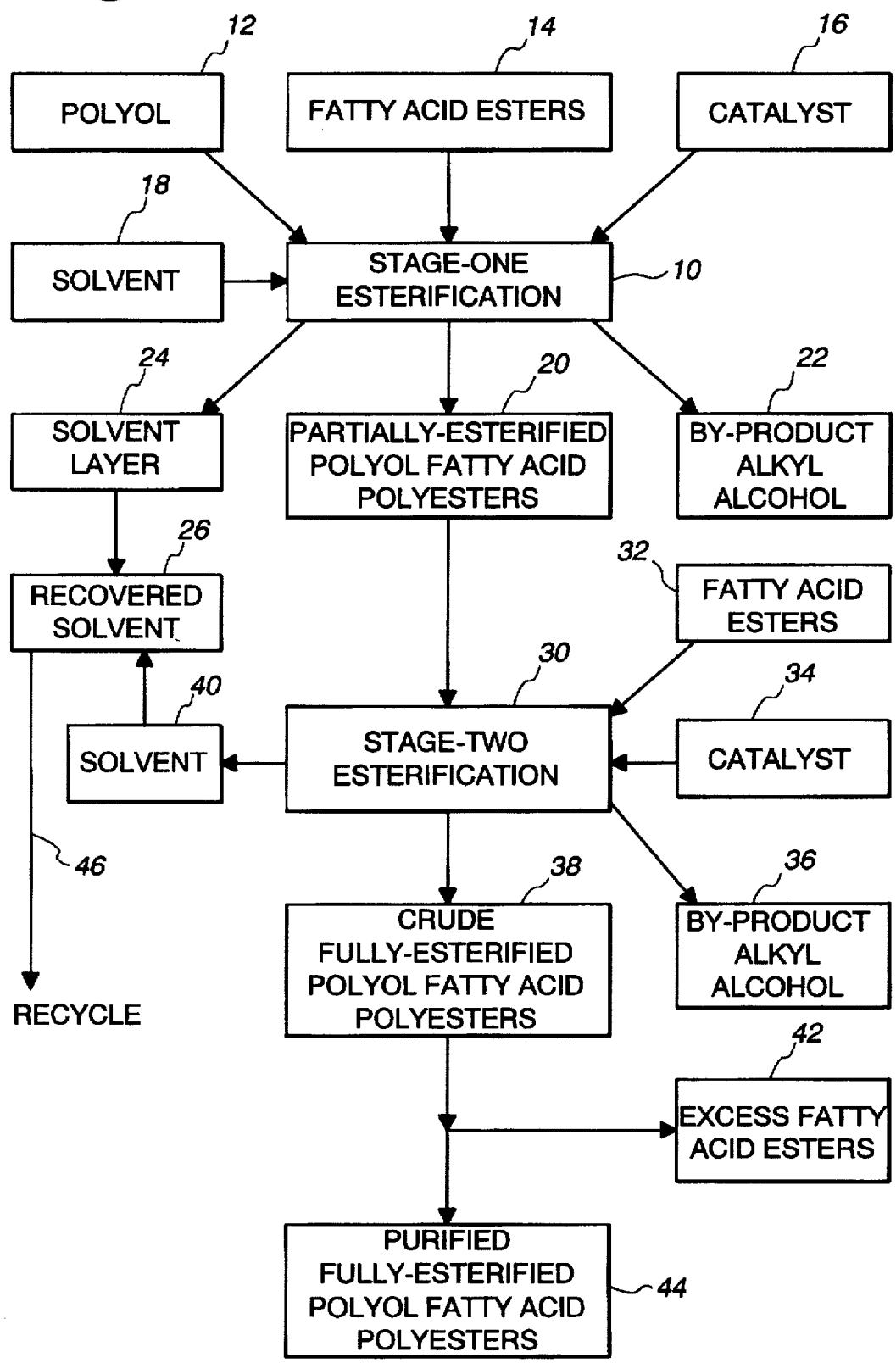
FIG. 2 is a flowchart generally illustrating the two-stage method of this invention.

FIG. 2 generally illustrates the two-stage process of the present invention. The starting polyol 12, fatty acid esters 14, catalyst 16, and solvent 18 are combined and reacted in stage-one esterification vessel 10 under relatively mild conditions while removing by-product lower alkyl alcohol 22. Once the desired partially-esterified polyol fatty acid polyesters 20 are obtained, they are separated from the solvent layer 24 using, preferably, phase separation techniques. The solvent layer 24 is preferably treated to recover the solvent 26. The partially-esterified polyol fatty acid polyesters 20, optional fatty acid esters 32, and catalyst 34 are combined and reacted in stage-two esterification vessel 30 under more rigorous conditions (relative to stage-one esterification) while removing by-product lower alkyl alcohol 34. During stage-two esterification, additional solvent 40 (which entered the stage-two esterification via the partially-esterified polyol fatty acid polyesters 20) is removed and, preferably, combined with recovered solvent 26 from the stage-one esterification. Preferably, recovered solvent 26 from both stage one and stage two is recycled via line 46 and reused as solvent 18 in the stage-one esterification 10. The crude fully-esterified polyol fatty acid polyester 38 is collected from the stage-two esterification 30 and then subjected to conventional purification techniques to provide purified fully-esterified polyol fatty acid polyesters 44. Preferably, excess (i.e., unreacted) fatty acid esters 42 from stage-two esterification 30 are also recovered and reused. The recovered fatty acid esters 42 can be recycled to the stage-one and/or stage-two esterifications 10 and 30. Purification preferably results in purified fully-esterified polyol fatty acid polyesters 44 containing less than about 2 ppm of solvent 18.

Generally, the polyol fatty acid polyesters, especially the saccharide fatty acid polyesters, and most especially the sucrose fatty acid polyesters produced by this invention are useful as fat substitutes or low-calorie fats. These polyol and saccharide fatty acid polyesters are especially useful since they have an especially high percentage of polyesters with essentially all of the hydroxyl groups from the starting polyol or saccharide being esterified with fatty acid groups. The saccharide fatty acid polyesters of the present invention are especially useful as fat substitutes or low-calorie fats in food products intended for human consumption. These saccharide fatty acid polyesters may be blended or incorporated into food compositions to reduce the overall calorie content of prepared food product. Liquid, semi-solid, or solid polyol or saccharide fatty acid polyesters (or combinations thereof) may be employed as fat substitutes. The solid polyol or saccharide fatty acid polyesters (i.e., melting points above about 37° C.) may also function as anti-anal leakage agents for use with the liquid polyol or saccharide fatty acid polyesters of this invention.

The following examples are provided to illustrate the invention and not to limit the invention. Unless specified otherwise, all percentages given in this specification are by weight.

Example 1. A rotary evaporator (Buchi model EL-131R) operating under refluxing conditions was used for the first stage reaction. Sucrose (10.12 g) and dimethylsulfoxide (DMSO; 85 g) in a 1000 ml flask attached to the rotary evaporator were mixed and refluxed at 90°±2° C. and 15 torr for about 20 minutes, with a condenser temperature of about 21° C., in order to remove traces of water. Methyl palmirate (100 g) and powdered potassium carbonate (1.04 g; 80 percent less than 325 mesh) were added to the reaction mixture; refluxing was continued using the same conditions for about 4 to 6 hours while volatile by-products were removed via the rotary evaporator. The resulting reaction mixture was transferred to a separatory funnel and allowed to stand at about 40° C. until the layer separated. The bottom layer, consisting mainly of solvent DMSO as well as color bodies and mono-, di-, and triesters, was drawn off. The nearly colorless upper layer contained the partially-esterified sucrose fatty acid polyesters (generally tetra and higher esters). The analysis of the partially-esterified sucrose fatty acid polyester was conducing using mass spectrometric (MS) and high performance liquid chromatographic (HPLC) techniques. The overall degree of substitution was about 5.6. The following typical results were obtained ("nd" in the tables means "not detected"):

|  | Analysis Results | |
|---|---|---|
|  | MS | HPLC |
| octaester | 29% | 91% |
| heptaester | 49% |  |
| hexaester | 18% |  |
| pentaester | 3% | 8% |
| tetraester | <0.5% | 1% |
| tri-, di-, & monoesters | nd | nd |

After removal of the DMSO by rotary evaporation, this partially-esterified sucrose fatty acid polyester was used in several second stage reactions wherein the catalyst form was varied. Into each of three 50 ml reaction flasks was placed 5.5 g of the partially-esterified sucrose fatty acid polyester and 6.2 g methyl stearate. Each flask was equipped with a stirrer, a reflux condenser jacketed at 45° C., and a nitrogen bleed line. The stirred reaction mixtures were heated to 130° C. using an oil bath. Once the reaction temperature reached 130° C., potassium carbonate catalyst (150 mg) was added. The catalyst was added in three different forms: (1) granular (average particle size about 500 µm), powdered (average particle size about 50 µm), and dissolved (an aqueous solution containing about 50 percent by weight catalyst). After catalyst addition, the reaction continued under reduced pressure (about 5 torr) for 18 hours. The following results were obtained:

|  | Catalyst Form | | |
|---|---|---|---|
|  | Granular | Powdered | Dissolved |
| Octaester | 45% | 52% | 64% |
| Heptaester | 40% | 37% | 31% |
| Hexaester | 11% | 9% | 5% |
| Pentaester | 3% | 2% | nd |
| Tetra- & Lower Esters | 1% | <1% | nd |

Although the second-stage reaction was not complete at the end of 18 hours, it is clear that the form of the catalyst plays a significant role. Generally, increasing the effective surface area of the catalyst increases the overall yield of the higher polyesters under similar reaction conditions. Moreover, these results demonstrate that the second stage reaction is at least tolerant of the water used to introduce the catalyst.

Example 2. This example illustrates the effect of the addition of potassium carbonate catalyst in aqueous solutions of different concentrations. The first and second stage reactions were carried out essentially as described in Example 1 except for catalyst addition in the second state reaction and for the use of a nitrogen sparge system in the second stage reaction to remove by-products. In the second stage, the same total amount of catalyst was added as in Example 1 (about 1.3 weight percent); the catalyst, however, was added as a 70 percent, 40 percent, or 10 percent aqueous solution. The second stage reaction mixtures were sampled at 6 and 21 hours and analyzed by mass spectroscopy. The following results were obtained:

|  | Concentration of Aqueous Catalyst | | | | | |
|---|---|---|---|---|---|---|
|  | 70% | | 40% | | 10% | |
|  | 6 hr | 21 hr | 6 hr | 21 hr | 6 hr | 21 hr |
| Octaester | 49% | 66% | 37% | 73% | 76% | 81% |
| Heptaester | 39% | 29% | 42% | 24% | 21% | 17% |
| Hexaester | 9% | 5% | 15% | 3% | 3% | 2% |
| Pentaester | 3% | nd | nd | nd | nd | nd |
| Tetra- & Lower Esters | <1% | nd | nd | nd | nd | nd |

The most dilute catalyst solution (10 percent) was the most effective, providing over 70 percent octaester in only 6 hours reaction time. Although not wishing to be limited by theory, the addition of more water per unit of catalyst may result in a more violent flashing off of the water and, thus, a higher surface area catalyst.

Example 3. Both the first and second stage reactions were carried out in a single 2-liter cylindrical reaction vessel. The reaction temperature was controlled with a heating mantle with a temperature controller and a thermocouple in the reaction mixture. The reaction pressure was controlled with a vacuum pump and a capillary metering-type "bleed" valve. The reaction mixture was stirred with a variable speed turbine-type stirrer. A nitrogen sparge, controlled with a rotometer with an inlet pressure of about 30 psig, is used to remove by-products. The reaction system allows introduction of an aqueous catalyst solution (used in second stage only) via a fine-bore tubing having one end immersed under the reaction mixture under a reduced pressure and the other end immersed in the catalyst solution at atmospheric pressure; the catalyst solution can be added without otherwise disturbing the system. The reaction system can be operated under reflux and distillation conditions without disrupting the reaction. Refluxing and distillation are achieved using a condenser cooled to about 18° C.

First Stage Reaction. Granular sucrose (50.6 g) and DMSO (412.6 g) were added to the reactor and then heated to about 90° C. at a pressure of about 20 torr, a sparge rate of about 2 ml/min/g reactant, and a stirrer speed of about 460 rpm, for about 30 minutes. Soybean methyl esters (500 g) and finely powdered potassium carbonate (5.2 g) were added. The reaction was allowed to proceed for about 5 hours under the just-stated reaction conditions (except that the sparge rate was increased to about 5 ml/min/g reactant) under reflux conditions (about 3 percent of the DMSO passed through the reactor and was collected in a cold trap protecting the vacuum pump). After the 5 hour reaction period, the reaction mixture was allowed to cool to room temperature by standing undisturbed overnight.

During cooling overnight, the reaction mixture separated into two layers. The darkly-colored DMSO layer, which contained about 88 percent of the total DMSO used in the first stage, was drained away. If desired, the DMSO in the lower layer could be recovered for reuse. The lightly-colored upper layer, which was retained in the reactor, was analyzed and found to contain mainly sucrose fatty acid polyesters and unreacted soybean methyl esters with traces of residual solvent and insoluble particulate material. The sucrose fatty acid polyester contained about 49 percent octaester, about 37 percent heptaester, about 11 percent hexaester, and about 2 percent pentaester.

Second Stage Reaction. The sucrose fatty acid polyester from the first stage reaction, and still contained in the reaction vessel, was heated to about 130° C. under distillation conditions using a pressure of about 5 torr, a sparge rate of about 5 ml/min/g reactant, and stirrer speed of about 460 rpm. When most of the residual DMSO was removed by distillation, about 6.1 g of potassium carbonate in a 20 percent aqueous solution was added through the thin-bore tubing at a rate of about 0.002 g solution/min/g reactants. After addition of the catalyst, the reaction system was returned to the reflux mode and the collection vessel (containing mostly DMSO and water from the catalyst addition) was removed from the system. The reaction was allowed to continue for about 24 hours at about 130° C. under reflux conditions using a pressure of about 5 torr, a sparge rate of about 5 ml/min/g reactant, and stirrer speed of about 460 rpm.

After the 24 hour reaction period, the residual catalyst was removed by filtration from the hot reaction mixture using a filtering aid. The filtered reaction mixture was an oily light yellow liquid (about 440 g) which, upon analysis, was found to contain mainly fully-esterified sucrose fatty acid polyesters, unreacted soybean methyl esters (about 23 percent), and traces of residual solvent. The fully-esterified sucrose fatty acid polyesters contained about 84 percent octaester, about 12 percent heptaester, and about 4 percent hexaester.

Example 4. Example 3 was repeated in all material aspects except that the addition of catalyst in the second stage reaction was modified. Rather than adding the catalyst as an aqueous solution, powdered potassium carbonate catalyst was added as a suspension in DMSO. The powdered potassium carbonate catalyst (about 6.2 g; 80 percent less than 325 mesh) was suspended in a small amount of DMSO (about 20 ml) and then added to the second stage reaction via the fine-bore tubing. Otherwise, both the first and second stage reactions were carried out in the same manner as in Example 3 and essentially equivalent results were obtained.

Example 5. The example illustrates the preparation of a sucrose fatty acid polyester having approximately the same functionality as butterfat. A blend of fatty acid methyl esters (FAMEs) derived from various hydrogenated triglycerides was used to achieve the desired fatty acid functionality.

Preparation of FAMEs. Suitable FAMEs were derived from a fully hydrogenated soybean oil and two partially hydrogenated soybean oils having the following fatty acid compositions:

|  | Fully Hyd. Oil | Partially Hyd. Oil #1 | Partially Hyd. Oil #2 |
|---|---|---|---|
| Palmitic | 11% | 10% | 10% |
| Stearic | 89% | 11% | 6% |
| Oleic | 0 | 64% | 73% |
| Linoleic | 0 | 15% | 11% |
| % Trans | — | 30–35% | 60–65% |

The "% trans" in the above table is the percentage of total unsaturated fatty acids.

The FAMEs were prepared by melting the respective oils (3000 g) in a 20-liter flask at 70° C. and then adding 1 percent by weight NaOH in methanol (450 g of solution), followed by an additional 1050 g methanol. The reaction mixture was refluxed for 4 hours at 68° C. with stirring, after which the basic catalyst was neutralized with phosphoric acid. The upper FAME layer was separated from the bottom methanol layer and then further treated in a rotary evaporation to remove residual methanol. The collected FAMEs were treated to an alkali extraction using a 15 percent aqueous NaOH solution to reduce the residual free fatty acid content to less than about 0.1 percent. The extracted FAMEs were further purified by distillation using a short path distillation apparatus.

First Stage Reaction. Sucrose (30 g) and DMSO (250 g) were mixed in a rotary evaporator at 90° C. and 20 torr; after about 30 minutes, the sucrose was completely dissolved. A mixture of FAMEs (310 g), followed by powdered potassium carbonate (3 g), was added to the sucrose/DMSO solution. The FAME mixture contained about 30 percent FAMEs derived from the fully hydrogenated soybean oil, about 35 percent FAMEs derived from the partially hydrogenated soybean oil #1, and about 35 percent FAMEs derived from the partially hydrogenated soybean oil #2. The reaction was continued for about 5 hours at 90° C. under reduced pressure suitable to maintain the DMSO under continuous reflux. The reaction mixture was then transferred to a separatory funnel where the layers were allowed to separate for about 16 hours at 50° C. The DMSO layer was separated and discarded. The top layer was filtered to remove residual catalyst and distilled at 70° C. and 0.2 torr to remove residual DMSO. The resulting top layer consisted mainly of partially-esterified sucrose fatty acid polyesters and unreacted FAMEs. The partially-esterified sucrose fatty acid polyesters was determined by mass spectrometry to have an average degree of substitution of about 6.3 and to contain about 11 percent octaester, 34 percent heptaester, 38 percent hexaester, 13 percent pentaester, 4 percent tetraester, and non-detectable levels of lower esters.

Second Stage Reaction. About 300 g of the top layer from the stage one reaction (consisting mainly of partially-esterified sucrose fatty acid polyesters and unreacted FAMEs) was placed in a 1000 ml round bottom flask. The top layer contained about a 2.3 fold molar excess of FAMEs, relative to the available hydroxyl groups in the partially-esterified sucrose fatty acid polyester. Thus, additional FAMEs were not required in this second stage reaction. The reaction system was equipped with a nitrogen sparge to remove by-products and a 250 mm Vigreux column operated under reflux conditions. The reaction mixture was heated to 130° C. under 5 torr pressure before the addition of a potassium carbonate catalyst. The catalyst was added as an aqueous solution (about 20 ml of a 20 percent potassium carbonate solution) through a thin-bore tube directly into the hot reaction mixture. The reaction was continued for 24 hours.

After completion of the reaction, the catalyst was removed by filtration and the residual FAMEs were reduced to below about 0.1 percent by molecular distillation. The resulting fully-esterified sucrose fatty acid polyester was analyzed by mass spectrometry and found to consist of about 94 percent octaester, 4 percent heptaester, 2 percent hexaester, and no detectable lower esters.

That which is claimed is:

1. A method for making a fully-esterified polyol fatty acid polyester, said method comprising a first-stage reaction and a second-stage reaction:

wherein the first-stage reaction comprises:

(1) reacting a polyol having at least four hydroxyl groups with a first fatty acid lower alkyl ester composition in the presence of a first alkaline salt catalyst and a solvent at a reduced pressure and a temperature of less than about 105° C. while removing by-product lower alkyl alcohol until a partially-esterified polyol fatty acid polyester is formed which has, on average, at least 50 percent of the hydroxyl groups in the polyol esterified with fatty acid groups from the first fatty acid lower alkyl ester composition; and (2) separating the partially-esterified polyol fatty acid polyester from the solvent; and wherein the second-stage reaction comprises:

(1) reacting the separated partially-esterified polyol fatty acid polyester with a second fatty acid lower alkyl ester composition, in the presence of a second alkaline salt catalyst and in the absence of any additionally-added solvent, at a reduced pressure and a temperature of greater than about 110° C. while removing by-product lower alkyl alcohol until a fully-esterified polyol fatty acid polyester is formed which contains at least 70 percent by weight polyol fatty acid polyesters in which all hydroxyl groups of the polyol are esterified with fatty acid groups from either the first or second fatty acid lower alkyl ester compositions; and (2) collecting the fully-esterified polyol fatty acid polyester.

2. A method as defined in claim 1, wherein the second fatty acid lower alkyl ester composition comprises from 0 to 100 percent by weight of the first fatty acid lower alkyl ester composition which is carried over from the first-stage reaction.

3. A method as defined in claim 1, wherein the polyol is a saccharide having at least six hydroxyl groups and the solvent is dimethylsulfoxide.

4. A method as defined in claim 3, wherein the polyol is sucrose.

5. A method as defined in claim 3, wherein the collected fully-esterified polyol fatty acid polyester is purified to contain less than about 2 ppm of the solvent used in the first-stage reaction.

6. A method as defined in claim 3, wherein the separated solvent from the first-stage reaction is purified sufficiently for reuse in the first-stage reaction and wherein the purified solvent is recycled to the first-stage reaction.

7. A method as defined in claim 1, wherein the polyol is sucrose.

8. A method as defined in claim 1, wherein the lower alkyl groups in the first and second fatty acid lower alkyl ester compositions are methyl groups and the by-product lower alkyl alcohols in the first-stage and second-stage reactions are methanol.

9. A method as defined in claim 1, wherein the lower alkyl groups in the first and second fatty acid lower alkyl ester compositions are ethyl groups and the by-product lower alkyl alcohols in the first-stage and second-stage reactions are ethanol.

10. A method as defined in claim 1, wherein the first-stage reaction is carried out at a pressure of about 1 to 50 torr and a temperature of about 60° to 105° C.

11. A method as defined in claim 10, wherein the second-stage reaction is carried out at a pressure of about 0.5 to 50 torr and a temperature of about 110° to 150° C.

12. A method as defined in claim 9, wherein the first and second alkaline salt catalysts are potassium carbonate and wherein the second alkaline salt catalyst is added as an aqueous solution such that the water is essentially flashed off upon addition.

13. A method as defined in claim 12, wherein the by-product lower alkyl alcohol in the first-stage reaction is removed immediately after formation using vacuum.

14. A method as defined in claim 12, wherein the by-product lower alkyl alcohols in both the first-stage reaction and the second-stage reaction are removed immediately after formation using combined vacuum and vigorous inert gas stripping or sparging.

15. A method as defined in claim 14, wherein the first fatty acid lower alkyl ester composition consists predominately of esters with relatively short fatty acid groups and the second fatty acid lower alkyl ester composition consists predominately of esters with relatively long fatty acid groups.

16. A method as defined in claim 15, wherein the collected fully-esterified polyol fatty acid polyester is further purified to contain less than about 2 ppm of the solvent used in the first-stage reaction.

17. A method as defined in claim 16, wherein the separated solvent from the first-stage reaction is purified sufficiently for reuse in the first-stage reaction and wherein the purified solvent is recycled to the first-stage reaction.

18. A method as defined in claim 1, wherein the first and second alkaline salt catalysts are potassium carbonate and wherein the second alkaline salt catalyst is added as an aqueous solution such that the water is essentially flashed off upon addition of the second alkaline salt catalyst.

19. A method as defined in claim 1, wherein the by-product lower alkyl alcohol in the first-stage reaction is removed immediately after formation using vacuum.

20. A method as defined in claim 1, wherein the by-product lower alkyl alcohols in both the first-stage reaction and the second-stage reaction are removed immediately after formation using combined vacuum and vigorous inert gas stripping or sparging.

21. A method as defined in claim 1, wherein the first fatty acid lower alkyl ester composition consists predominately of esters with relatively short fatty acid groups and the second fatty acid lower alkyl ester composition consists predominately of esters with relatively long fatty acid groups.

22. A method as defined in claim 1, wherein the collected fully-esterified polyol fatty acid polyester is purified to contain less than about 2 ppm of the solvent used in the first-stage reaction.

23. A method as defined in claim 1, wherein the separated solvent from the first-stage reaction is purified sufficiently for reuse in the first-stage reaction and wherein the purified solvent is recycled to the first-stage reaction.

24. A method for making a fully-esterified sucrose fatty acid polyester, said method comprising a first-stage reaction and a second-stage reaction:

wherein the first-stage reaction comprises:
(1) reacting sucrose with an excess of a first fatty acid methyl ester composition, in the presence of a first alkaline salt catalyst and a solvent selected from the group consisting of dimethylacetamide, dimethylformamide, and dimethylsulfoxide, at a reduced pressure of about 1 to 50 torr and a temperature of about 40° to 105° C. while removing methanol by-product until a partially-esterified sucrose fatty acid polyester is formed which has, on average, at least 50 percent of the hydroxyl groups in the sucrose esterified with fatty acid groups from the first fatty acid methyl ester composition; and
(2) separating the partially-esterified sucrose fatty acid polyester from the solvent; and wherein the second-stage reaction comprises:
(1) reacting the separated partially-esterified sucrose fatty acid polyester with a second fatty acid methyl ester composition, in the presence of a second alkaline salt catalyst and in the absence of any additionally-added solvent, at a reduced pressure of about 0.5 to 50 torr and a temperature of about 110° to 150° C. while removing methanol by-product until a fully-esterified sucrose fatty acid polyester is formed which contains at least 70 percent by weight sucrose fatty acid polyesters in which all hydroxyl groups of the sucrose are esterified with fatty acid groups from either the first or second fatty acid methyl ester compositions; and
(2) collecting the fully-esterified sucrose fatty acid polyester.

25. A method as defined in claim 24, wherein the second fatty acid lower methyl ester composition comprises from 0 to 100 percent by weight of the first fatty acid lower methyl ester composition which is carried over from the first-stage reaction.

26. A method as defined in claim 24, wherein the solvent is dimethylsulfoxide and wherein the methanol by-product in the first-stage is removed immediately after formation using vacuum.

27. A method as defined in claim 26, wherein the first and second alkaline salt catalysts are potassium carbonate and wherein the second alkaline salt catalyst is added as an aqueous solution such that the water is essentially flashed off upon addition of the second alkaline salt catalyst.

28. A method as defined in claim 27, wherein the partially-esterified sucrose fatty acid polyester has an average degree of substitution of about 5 to 7 and wherein the fully-esterified sucrose fatty acid polyester contains at least 85 percent by weight sucrose fatty acid polyesters in which essentially all hydroxyl groups of the sucrose are esterified with fatty acid groups from either the first or second fatty acid methyl esters compositions.

29. A method as defined in claim 28, wherein the collected fully-esterified sucrose fatty acid polyester is purified to contain less than about 2 ppm of the solvent used in the first-stage reaction.

30. A method as defined in claim 24, wherein the solvent is dimethylsulfoxide and wherein the methanol by-products in both the first-stage and second-stage reactions are removed immediately after formation using combined vacuum and vigorous inert gas stripping or sparging.

31. A method as defined in claim 30, wherein the first and second alkaline salt catalysts are potassium carbonate and wherein the second alkaline salt catalyst is added as an aqueous solution such that the water is essentially flashed off upon addition of the second alkaline salt catalyst.

32. A method as defined in claim 31, wherein the partially-esterified sucrose fatty acid polyester has an average degree of substitution of about 5 to 7 and wherein the fully-esterified sucrose fatty acid polyester contains at least 85 percent by weight sucrose fatty acid polyesters in which essentially all hydroxyl groups of the sucrose are esterified with fatty acid groups from either the first or second fatty acid methyl esters compositions.

33. A method as defined in claim 32, wherein the collected fully-esterified sucrose fatty acid polyester is purified to contain less than about 2 ppm of the solvent used in the first-stage reaction.

34. A method as defined in claim 24, wherein the first and second alkaline salt catalysts are potassium carbonate and wherein the second alkaline salt catalyst is added as an aqueous solution such that the water is essentially flashed off upon addition of the second alkaline salt catalyst.

35. A method as defined in claim 34, wherein the solvent and the partially-esterified sucrose fatty acid polyester produced in the first-stage reaction form separate layers and the partially-esterified sucrose fatty acid polyester is separated from the solvent by separating the layers.

36. A method as defined in claim 34, wherein the first fatty acid methyl ester composition consists predominately of esters with relatively short fatty acid groups and the second fatty acid methyl ester composition consists predominately of esters with relatively long fatty acid groups.

37. A method as defined in claim 36, wherein the partially-esterified sucrose fatty acid polyester is separated from the solvent by adding water to form a partially-esterified sucrose fatty acid polyester layer and a solvent layer and then separating the layers.

38. A method as defined in claim 24, wherein the solvent and the partially-esterified sucrose fatty acid polyester produced in the first-stage reaction form separate layers and the partially-esterified sucrose fatty acid polyester is separated from the solvent by separating the layers.

39. A method as defined in claim 24, wherein the first fatty acid methyl ester composition consists predominately of esters with relatively short fatty acid groups and the second fatty acid methyl ester composition consists predominately of esters with relatively long fatty acid groups.

40. A method as defined in claim 39, wherein the partially-esterified sucrose fatty acid polyester is separated from the solvent by adding water to form a partially-esterified sucrose fatty acid polyester layer and a solvent layer and then separating the layers.

41. A method as defined in claim 24, wherein the partially-esterified sucrose fatty acid polyester has an average degree of substitution of about 5 to 7 and wherein the fully-esterified sucrose fatty acid polyester contains at least 85 percent by weight sucrose fatty acid polyesters in which essentially all hydroxyl groups of the sucrose are esterified with fatty acid groups from either the first or second fatty acid methyl ester compositions.

42. A method as defined in claim 24, wherein the collected fully-esterified sucrose fatty acid polyester is purified to contain less than about 2 ppm of the solvent used in the first-stage reaction.

* * * * *

UNITED STATES PATENT AND TRADEMARK OFFICE
CERTIFICATE OF CORRECTION

PATENT NO. : 5,681,948
DATED : October 28, 1997
INVENTOR(S) : Miller et al.

It is certified that error appears in the above-indentified patent and that said Letters Patent is hereby corrected as shown below:

Claim 12, Column 18, line 63, change the dependency from "9" to --11--.

Claim 24, Column 19, line 57, change "40°" to --60°--.

Signed and Sealed this

Twenty-fourth Day of March, 1998

Attest:

BRUCE LEHMAN

Attesting Officer

Commissioner of Patents and Trademarks